United States Patent [19]

Kobayashi

[11] Patent Number: 4,461,168
[45] Date of Patent: Jul. 24, 1984

[54] HYDROGEN EMBRITTLEMENT TESTER

[76] Inventor: Masami Kobayashi, 3-13-15, Hachimanyama, Setagaya-ku, Tokyo, Japan

[21] Appl. No.: 400,693

[22] Filed: Jul. 22, 1982

[30] Foreign Application Priority Data

Mar. 8, 1982 [JP] Japan .................................. 57-35211

[51] Int. Cl.³ .............................................. G01N 3/20
[52] U.S. Cl. ......................................... 73/87; 73/851
[58] Field of Search ................... 73/87, 851, 853, 818

[56] References Cited

U.S. PATENT DOCUMENTS 3,455,152 7/1969 Maker ..................................... 73/87

*Primary Examiner*—Anthony V. Ciarlante
*Attorney, Agent, or Firm*—Armstrong, Nikaido, Marmelstein & Kubovcik

[57] ABSTRACT

A hydrogen embrittlement tester, for a metal sample, has a vise device for holding the sample.

For testing bend fracture, the distance between both ends of the sample is measured, which corresponds to that of the distance between the sample holding members. For testing the delayed fracture, the time from when the sample is held until it is fractured is measured.

An electric path is formed between the sample holding members and the sample only when the sample is held so that measurement can be automatically stopped when the sample is fractured.

6 Claims, 2 Drawing Figures

4,461,168

HYDROGEN EMBRITTLEMENT TESTER

FIELD OF THE INVENTION

The present invention relates to a hydrogen embrittlement tester which can be used in the bend fracture test and the delayed fracture test of a metal sample, such as high tensile steel.

BACKGROUND OF THE INVENTION

Hydrogen embrittlement generally occurs in metal as a result of pickling, electroplating, or other treatment. In this phenomenon, the metal absorbs slight amounts of hydrogen and becomes brittle and easily fractured. This remarkably occurs in steels having great tensile strength and hardness.

No conventional testers have been found satisfactory for testing the rate of hydrogen embrittlement resulting from the surface treatment such as described above. A tester able to do this, therefore, has been much awaited.

SUMMARY OF THE INVENTION

It is an object of the present invention to provide a hydrogen embrittlement tester.

A hydrogen embrittlement tester according to the present invention comprises a vise device having a pair of opposed members for holding the sample and an electrically conductive plate means mounted on the opposed edges of said members via insulating materials. An electric path can be formed between the plates and the metal sample. This arrangement in effect serves as an automatic switch. The switch is turned on when the sample is held and is turned off when the sample is fractured. To give stress to the sample, one of the opposed members is movable. The two members can therefore be brought close to or away from each other. An actuating means for this member is provided, which preferably comprises a reversible motor and a feed screw connected to the motor, the feed screw being mated with a threaded hole of this member.

The tester further comprises measuring means. The indispensable items of hydrogen embrittlement test are the bend fracture test and the delayed fracture test, the delayed fracture being the test of the phenomenon of the sample being suddenly fractured a certain time after being held under a certain load. The measuring means, therefore, includes means for measuring the distance between both members, for the bend fracture test, and means for measuring the time from when the sample is held between both members until it is fractured, for the delayed fracture test. These two means are operable only when the above electric path appears.

Other features and advantages will become apparent from the following description of a preferred embodiment, with reference to the accompanying drawings.

DESCRIPTION OF A PREFERRED EMBODIMENT

Figure 1:
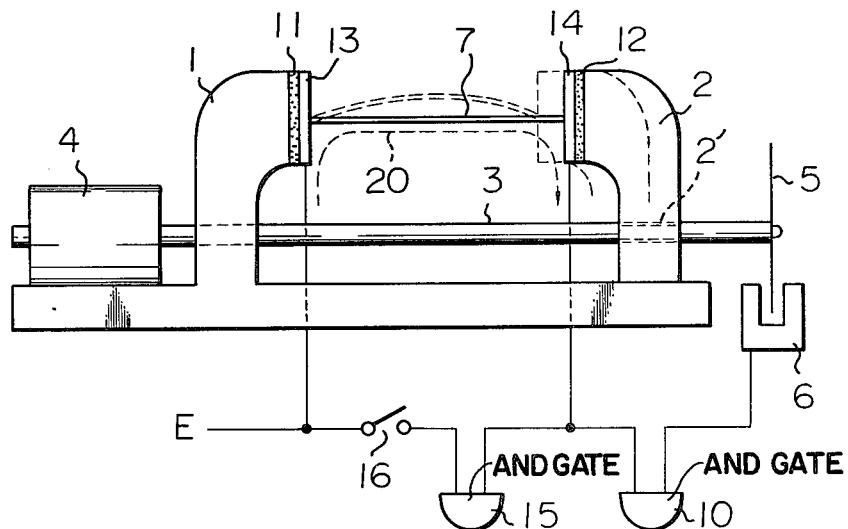
FIG. 1 is a schematic view of a preferred embodiment of a hydrogen embrittlement tester, according to the present invention.
Figure 2:
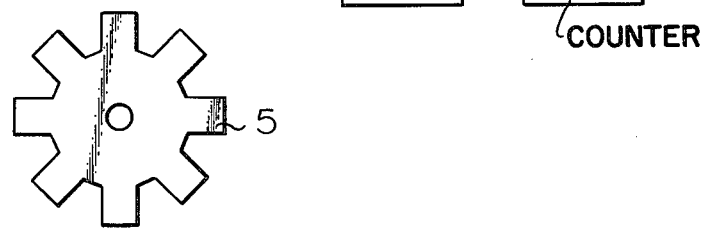
FIG. 2 is a front view of the chopper used in the tester of FIG. 1.

FIG. 1 shows a hydrogen embrittlement tester, according to the present invention. The tester has a pair of opposed holding members 1 and 2 for a sample 7. Member 1 is rigidly fixed to the tester body. Member 2 is slidably secured to the tester body. A threaded hole 2' is provided in the movable member 2. A feed screw 3 is mated with and extends through the threaded hole 2'. The feed screw 3 is connected to a reversible motor 4 for actuating the movable member 2. Rotation of the feed screw 3, therefore, changes the distance between both members 1 and 2. This arrangement is known as a vise device. A plate or chopper 5 is carried on the feed screw 3 at its one end. An example of the plate 5 is shown in FIG. 2. The plate 5 incorporates a photocoupler 6 which comprises a light emission diode and a phototransistor. When the feed screw 3 rotates, circumferential projections of the plate 5 pass through the gap between the light emission diode and the phototransistor. The photocoupler 6 then outputs the pulse voltages corresponding to the rotating degrees of the feed screw 3.

On the opposed surfaces of the holding members 1 and 2, high electric conductive plates 13, 14 are bonded via insulating layers 11, 12, respectively. Thus, an electric path 20 is formed, which electrically connects one of the high electric conductive plate 13, 14 to the other via metal sample 7 when sample 7 is held therebetween.

A counter 8 and a timer 9 are further provided. The counter 8 is electrically connected to AND gate 10 which receives the output of the photocoupler 6 and the voltage E throught the electric path 20. The timer 9 is electrically connected to AND gate 15 which receives the voltage E through the electric path 20 and the same voltage E through an electric path having a manual switch 16.

In operation, the sample 7 to be tested is first placed between the plates 13 and 14 of the holding members 1 and 2. The motor 4 is driven until sample 7 is held at a relatively low load so that the sample will not deflect greatly or slip down. Then, the counter 8 is reset at a starting point (such as 0000 or 1000). The bend fracture test is started by driving the motor 4 which causes the movable member 2 to move toward the rigid member 1 via the feed screw 3, the sample to be tested being gradually bent. The counter 8 counts the degrees of rotation of the feed screw 3, which is proportional to the distance between the two holding members, that is, the distance between the ends of the sample 7 held between the members. Subsequently, the sample will be fractured and will slip down from the holding members. At this instant, the voltage through the electric path 20 will disappear and the counter 8 will be switched off. The rate of the bend fracture is normally shown by the percentage of the distance between the edges of the sample when it is fractured per the original length thereof. This test apparatus is therefore suitable for the bend fracture test.

In the delayed fracture test, the sample to be tested is held in a similar way as the bend fracture test. The timer 9 as well as the counter 8 is reset. The motor 4 is driven until the counter shows the desired value. The motor 4 is then stopped and the switch 16 is closed by operator. The delayed fractured test is started by leaving the sample in that condition under the static load. The sample will be fractured in a time representing the degree of embrittlement of each sample. The timer 9 is stopped when the voltage through the electric path 20 disappears. Therefore, there is no need to watch the sample until it is fractured.

It is apparent from the foregoing description, that a hydrogen embrittlement tester according to the present invention can be applied to both the bend fracture test and the delayed fracture test.

I claim:

1. A hydrogen embrittlement tester for a metal sample comprising:

a vise device having a pair of opposed members for holding the sample therebetween, electrically conductive plate means mounted on the opposed edges of said members via insulating material for forming an electric path between both plate means through the sample to be tested;

first means for actuating one of said members such that the members are brought close to or away from each other;

second means for measuring the distance between said members; and third means for measuring the time from when the sample is held between said members until it is fractured, said second and third means being operable only when the sample is held between said members.

2. A tester according to claim 1, wherein said first means comprises a reversible motor and a feed screw connected to said motor, said feed screw being mated with a threaded hole of said one of the members.

3. A tester according to claim 2, wherein a fourth means is provided for measuring the degrees of rotation of said feed screw.

4. A tester according to claim 3, wherein said fourth means comprises a photocoupler and chopper means carried on said feed screw and associated with said photocoupler.

5. A tester according to claim 4, wherein said second means comprises a counter which is driven by the output from an AND gate receiving two inputs, one being the signal from said photocoupler and the other being the signal through the electric path consisting of said opposed edges of said members and the sample held therebetween.

6. A tester according to any one of the preceding claims, wherein said third means comprises a timer which is operated by the output from an AND gate receiving two inputs, one being the signal through the electric path consisting of said opposed edges of said members and the sample held therebetween and the other being the signal through a normally open switch which is closed when the measuring is to be started.

* * * * *